United States Patent [19]

Chuang

[11] Patent Number: 4,689,379
[45] Date of Patent: Aug. 25, 1987

[54] HAIR TREATING RESINS
[75] Inventor: Jui-Chang Chuang, Wayne, N.J.
[73] Assignee: GAF Corporation, Wayne, N.J.
[21] Appl. No.: 6,404
[22] Filed: Jan. 23, 1987
[51] Int. Cl.⁴ .............................................. C08F 20/10
[52] U.S. Cl. ...................................... 526/282; 424/47
[58] Field of Search ........................... 526/282; 424/47
[56] References Cited
U.S. PATENT DOCUMENTS
4,503,185 3/1985 Hausman ............................. 526/282
4,599,378 7/1986 Hausman ............................. 526/282

Primary Examiner—Paul R. Michl
Attorney, Agent, or Firm—Marilyn J. Maue; Joshua J. Ward

[57] ABSTRACT

An improved hair spray resin comprising microspheres of vinyl acetate/mono-n-$C_4$–$C_5$ alkyl maleate/ an isobornyl acrylate terpolymer in a molar ratio of about 1:0.35–1:0.05–0.25 and a one-step suspension polymerization process for the preparation of said resin in yields above 85%.

20 Claims, No Drawings

HAIR TREATING RESINS

In one aspect, this invention relates to an improved hair spray resin, particularly adapted for use in aerosol and pump formulations, having excellent hair holding capacity under conditions of high humidity and improved compatibility with alcohols and hydrocarbon propellants. In another aspect, the invention relates to a suspension polymerization for the preparation of microspheric particles of said improved resins in high yields.

Generally, effective hair spray formulations and film forming resins must satisfy a rigid set of requirements. Specifically, the resulting films should remain non-tacky in humid atmosphere but should be easily removable in aqueous soap solutions or shampoos. The films should have high hair cohesivity and yet possess sufficient strength and elasticity so as to avoid dusting or flaking when the hair is subjected to varying stresses during combing or brushing. The resulting films should remain clear, transparent and glossy on ageing and are required to have a viscosity range which permits uniform spraying without nozzle clogging. Additionally, the hair spray resin should show little or no tendency to interact with perfume or other optional components conventionally utilized in hair spray formulations and should be readily soluble organic solvents while exhibiting good compatibility with conventional hydrocarbon propellants.

Many polymeric systems have been utilized in an attempt to meet these stringent requirements. Among these are included polyvinylpyrrolidone and copolymers of N-vinylpyrrolidone with vinyl acetate. However, these copolymers do not exhibit the desired degree of holding at high humidity. Moreover, several of the vinylpyrrolidone polymers possess an unpleasant odor. Vinyl ether/maleic half ester copolymers have also been used in hair sprays, but high molecular weight is required to achieve adequate holding. Additionally, vinyl acetate polymers having 15 to 35% of their acetate qroups converted to hydroxyl groups have been proposed for increasing solubility in carbon dioxide propellant systems. Unfortunately, such increased solubility is achieved at the cost of lowered holding power. Although each of the above resins meets at least some of the above cited requirements, none has exhibited all of these characteristics to a desired degree.

Accordingly, it is an object of the present invention to overcome the individual deficiencies of the above discussed polymers and to provide an improved alcohol soluble resin ideally suited for hair sprays in a particulate microspherical form.

It is another object of this invention to provide a convenient and economical process for the preparation of said resin.

Still another object of this invention is to provide a microspheric resin for use in hair sprays and having excellent hair holding capability, particularly under conditions of high humidity.

Another object is to provide an esteric resin formulation which eliminates spray can corrosion.

Another object is to provide a relatively high molecular weight esteric resin having improved propellant compatibility, excellent spray pattern, increased hair holding and a superior low cloud/clear temperature point.

These and other objects will become apparent from the following description and disclosure According to this invention there is provided a terpolymer resin of random or alternating structure comprising essentially a vinyl ester, a water insoluble or water miscible alkyl maleate half ester and the acrylate or methacrylate ester of a saturated hydroxylated bicyclic hydrocarbon in a molar ratio of about 1:0.35–1:0.05–0.25.

The proportions of monomers in the present resin are critical since it is found that, above 3.5:1 vinyl acetate to maleate half ester, the terpolymer becomes insoluble in commercial alcohol carriers such as ethanol and below 1:1 the terpolymer develops tact. It is also found that the high water sensitivity and/or low glass transition temperatures (Tg) of the vinyl ester and maleate half ester copolymers prevents their synthesis by the economical one step suspension polymerization of the present invention. Accordingly, the incorporation of an acrylate or methacrylate ester of a saturated, hydroxylated bicyclic hydrocarbon having a relatively high Tg, is an essential monomer in the terpolymeric compound. Acrylate and/or methacrylate esters of isoborneol, exo-norborneol and endo-norborneol are preferred and the isobornyl ester is the most preferred. The preferred bicyclic compounds are those having a hydrocarbon bridge and are generally defined by the formula

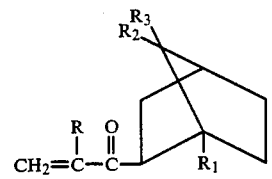

wherein each of R, $R_1$, $R_2$ and $R_3$ is hydrogen or methyl. These monomers minimize development of tack in the hair spray formulation. The isobornyl acrylate and isobornyl methacrylate, because of their high homopolymer Tg values, i.e. 90°–100° C. and 170° C., respectively, are particularly suitable for this purpose. In general, a Tg of from about 40° C. to about 100° C. is desirable in the present terpolymeric product.

According to this invention, the molar ratio of vinyl ester to the bicyclic acrylate or methacrylate monomer in the terpolymer should be between about 4:1 and about 20:1. A particularly preferred molar ratio of vinyl acetate/mono-n-$C_4$ to $C_5$ alkyl maleate/isobornyl acrylate or methacrylate is about 1:0.6–0.8:0.08–0.12, e.g. 1:0.75:0.1.

Illustrative of the water insoluble or water miscible alkyl maleate half ester monomers of this invention are the propyl, butyl, pentyl, hexyl, heptyl, octyl, nonyl and decyl half esters; although the n-butyl and n-pentyl half esters are the most preferred.

Examples of the vinyl ester monomeric component are those containing 4 to 14 carbon atoms which include vinyl acetate, vinyl propionate, vinyl isopropionate, vinyl isobutyrate, vinyl butyrate, vinyl hexanoate, vinyl pivalate, vinyl laurate and vinyl neodecanoate, of which vinyl acetate is the most preferred.

The present resin in the form of beads or microspheres prepared by suspension polymerization provides certain advantages. For example, the resin has a higher molecular weight for better hair holding under humid conditions and achieves the highest conversion, thus minimizing unreacted monomers. Additionally, the present resin in dry bead form can be handled and shipped safely in the absence of flammable alcohol solvents.

The microspheres of the present terpolymeric resin generally have an average diameter of between about 0.5 and about 2.5 mm when synthesized by the suspension polymerization process of the present invention and the polymer products possess a relative viscosity (RV) greater than 1.3. Below a relative viscosity of 1.3 the polymer lacks curl retention under humid conditions.

Generally, the suspension polymerization process comprises adding the monomers, individually or premixed in the above proportions, to a 0.1 to 2.0 % by weight aqueous suspension medium, preferably a 0.25 to 1.0 weight % solution, of a carboxylated polyelectrolyte, preferably methyl vinyl ether-maleic acid copolymer (GANTREZ® S-95), wherein they are polymerized in the presence of a free radical initiator under conditions of agitation at a temperature of between about 40° and about 90° C., preferably between about 50° and about 70° C. The initiator can be added to the monomer mixture before or after the monomers have been charged into the suspension medium. The reaction is executed in an inert atmosphere which can be maintained by purging with nitrogen to eliminate air and oxygen.

The polymerization reaction is carried out under constant agitation over a period of from about 4 to about 12 hours; although usually 6 to 8 hours is sufficient to complete the reaction and formation of a bead-like terpolymer product. The beads are then separated from the suspension medium, washed with water, and dried. The supernate separated from the product can be recycled to the reaction zone if desired as a make-up suspension media in which any unreacted monomer in the supernate can be converted, thus providing a highly efficient, pollution-free process.

Generally, the suspension medium can be any aqueous solution containing from about 0.1 wt. % to about 2.0 wt. % of a carboxylated polyelectrolyte suspending agent. Suitable suspending agents include methyl vinyl ether/maleic acid copolymer (e.g. GANTREZ® S-95)*; ethylene/maleic anhydride copolymer (e.g. EMA resin)**; vinyl acetate/maleic anhydride copolymer and N-vinyl-2-pyrrolidone/maleic anhydride copolymer*. The concentration of total monomers in the suspension medium can vary from about 10 wt. % to about 50 wt. %; however, concentrations of between about 20 and about 40 wt. % monomers are recommended from the standpoint of economics and process conditions.

* Supplied by GAF Corporation
** Supplied by Monsanto Co.

Generally, between about 0.05 wt. % and about 5.0 wt. % of initiator, based on total monomers of the terpolymer can be employed in the polymerization reaction; although, in most instances, between about 0.1 and about 2.0 wt. % initiator is sufficient to promote the reaction.

The free radical initiators employed in the present reaction are typically low temperature initiators having a half-life of 10 hours at temperatures between about 45° C. and about 65° C. although any of the free radical initiators which are effective at temperatures between about 40° C. and about 80° C. are suitably employed herein. Typical low temperature initiators include peroxyesters such as t-butylperoxypivalate (Lupersol® 11) and t-butylperoxyneodecanoate (Lupersol® 10), peroxydicarbonates such as di-(n-propyl)peroxydicarbonate (Lupersol® 221), di-(sec-butyl)peroxydicarbonate (Lupersol® 225) and di-(2-ethylhexyl)peroxydicarbonate (Lupersol® 223) all supplied by Penwalt Corporation. Also, azo initiators such as 2,2'-azobis(2,4-dimethylvaleronitrile), VAZO®-52 and 2,2'-azobis(2,4-dimethyl-4-methoxy-valeronitrile), VAZO®-33W, both supplied by duPont, are suitable.

The present terpolymeric resins are employed as the active ingredients in any of the standard hair treating formulations employed for pump and aerosol sprays. The resins can also be used to augment existing hair spray formulations to improve solubility, hair holding and hydrocarbon compatibility. When used as the sole active hair holding agent in the formulation, the present resins are employed in concentrations between about 0.5% and about 10% solids, preferably between about 2.0% and about 5.0% solids.

In preparing the hair treatment formulations, the resin is usually dissolved in an inert carrier, such as a lower alcohol, e.g. ethanol, an aqueous ethanol solution, isopropanol and, the like, etc. For aerosol sprays, the formulations also include a conventional propellant such as, for example, a 20/80 blend of propane/isobutane (Propellant A-46), nitrogen, nitrogen oxide, carbon dioxide, etc.

The formulations are charged into a canister and the propellant pressurized into the canister to provide a spray operated through a pressure release nozzle. The present resins have a long shelf life and avoid nozzle clogging or canister corrosion when employed in the above concentrations.

Having thus generally described the invention, reference is now had to the following examples which provide specific and preferred embodiments but which are not to be construed as limiting to the scope of the invention as more broadly described above and in the appended claims. All parts given are by weight unless otherwise indicated.

EXAMPLE 1

Into a four-necked, one-liter resin kettle, fitted with a mechanical agitator, a reflux condenser, a dropping funnel, thermometer and a nitrogen inlet tube was charged:

86.00 g. of vinyl acetate (1.00 mole)
103.20 g. of mono-n-butyl maleate (0.06 mole)
20.80 g. of isobornyl acrylate (0.10 mole) and
4.20 g. of t-butylperoxyneodecanoate
(Lupersol®-10 M 75; 75% active)

The contents of the kettle were mixed thoroughly by the mechanical agitator operating at about 250 rpm for a period of about 5 minutes, after which a polyelectrolyte solution prepared from 1.05 g. of GANTREZ® S-95 and 315.00 g. of distilled water was added.

The mixture was purged with nitrogen and gently heated to 62° C. over a period of 60 minutes while maintaining agitation and the nitrogen purge. The reactants were held at 62°–64° C. for 8 hours during which the bead-like resin product was formed. The mixture was then cooled to 15° C. in a water/ice bath and the supernate decanted. The remaining beads, having an average diameter of 0.5–1.0 mm, were washed twice with distilled water, filtered and then dried under house vacuum at ambient temperature for 8 hours, followed by drying in a hot air oven at 55°–60° C. for 24 hours.

The supernate separated from the crude product can be recycled to the reaction zone to provide a portion of the suspension medium, if desired.

The terpolymeric product, referred to as Polymer 1, in the form of microspheric particles and having the composition:

40.95% vinyl acetate (VAC)
49.14% mono-n-butyl maleate (MBM) and
9.91% isobornyl acrylate (IBA)

was recovered in 87.8% yield. This polymer has a relative viscosity of 1.66, a K-value of 49.6, a molecular weight of 370,000 (by gel permeation chromatography in tetrahydrofuran), an acid number of 129.4 mg. NaOH/g and a Tg of 70° C.

EXAMPLES 2-10

In Examples 2-10 the procedure identical to that described in Example 1, with the below noted modifications, was repeated to prepare Polymers 2-10.

Examples 2-7 were modified in that the weight ratios of the monomers and the polymerization initiators were altered as shown in Table I. Also, in Example 4 the GANTREZ® S-95 suspending agent was replaced by ethylene/maleic anhydride copolymer (EMA® resin). In Example 8, the isobornyl acrylate monomer and the t-butylperoxy neodecanoate initiator were replaced by isobornyl methacrylate and di-(2-ethylhexyl) peroxydicarbonate (Lupersol® 223 M75), respectively, and the weight ratios of the monomers were also varied as noted in Table I. In Example 9, the mono-n-butyl maleate monomer and the t-butylperoxyneodecanoate initiator were replaced by mono-n-pentyl maleate and di-(2-ethylhexyl) peroxydicarbonate (Lupersol® 223 M75), respectively, and the weight ratios of the monomers were also varied as noted. In Example 10, t-butylperoxvneodecanoate was replaced by Lupersol® 223 M75, mono-n-butyl maleate was replaced by a mixture of mono-n-butyl maleate and mono-n-pentyl maleate and the weight ratios of the monomers were also altered as noted.

Each of the polymeric products, i.e. Polymers 1-10, were analyzed and characterized as reported in following Table I.

EXAMPLE 11

This example illustrates the excellent solution properties of the hair spray resins of this invention.

Each resin of Examples 1-10 were evaluated for its solubility in ethanol without adding a neutralizing agent such as 2-amino-2-methyl-1-propanol (AMP). In these tests, 2.5 g. of each polymer were dissolved in 67.5 g. of anhydrous ethanol (SDA 40-2 grade) under agitation and the clarity of the solution was noted. For each clear solution, 30 g. of n-hexane were then added and the solubility in ethanol/n-hexane mixture was recorded. In this test, n-hexane was found to be an ideal substitute for evaluating the compatibility of resin with hydrocarbon propellant A-46 (blend of 20/80 propane/isobutane). The testing results were compared with Resyn® 28-2930* (available from National Starch and Chemical corporation) as shown in following Table II.

*Vinyl acetate/crotonic acid/vinyl neodecanoate terpolymer, a commercial hair spray resin from the National Starch and Chemical Corporation.

TABLE II

| Polymer | Solubility in Ethanol | Solubility in Ethanol/n-Hexane |
|---|---|---|
| Resyn® 28-2930 (control) | slightly hazy | hazy |
| 1 | clear | clear |
| 2 | clear | clear |
| 3 | clear | clear |
| 4 | clear | clear |
| 5 | clear | clear |
| 6 | clear | clear |
| 7 | clear | clear |
| 8 | clear | clear |
| 9 | clear | clear |
| 10 | clear | clear |

In addition, all of the polymers of this invention (Polymers 1-10) in the ethanol/n-hexane mixture remained clear at a temperature below −18° C. (0° F.) which is an indication of their excellent compatibility with hydrocarbon propellant for aerosol hair spray applications.

EXAMPLE 12

This example provides a representative formulation for an aerosol hair spray employing a typical hydrocar-

TABLE I

| Polymer | 1 | 2 | 3 | 4 | 5 | 6 | 7 | 8 | 9 | 10 |
|---|---|---|---|---|---|---|---|---|---|---|
| Vinyl Acetate (VAC) | 40.95 | 37.26 | 32.43 | 33.83 | 27.74 | 32.68 | 36.47 | 36.26 | 34.92 | 35. |
| Mono-n-butyl Maleate (MBM) | 49.14 | 44.71 | 51.89 | 57.99 | 55.48 | 56.03 | 54.71 | 54.38 | | 26. |
| Mono-n-pentyl Maleate (MPM) | | | | | | | | | 56.64 | 28. |
| Isobornyl Acrylate (IBA) | 9.91 | 18.03 | 15.68 | 8.18 | 16.78 | 11.29 | 8.82 | | 8.44 | 8.62 |
| Isobornyl Methacrylate (IBMA) | | | | | | | | 9.36 | | |
| t-Butylperoxy neodecanoate (Lupersol® 10M75), % | 1.50 | | | | | | | | | |
| t-Butylperoxypivalate (Lupersol® 11), % | | 1.00 | | | | | | | | |
| Di-(2-ethylhexyl) peroxydicarbonate (Lupersol® 223M75) | | | 1.00 | 1.00 | 1.00 | 1.00 | 1.00 | 1.00 | 1.00 | 1.00 |
| GANTREZ® S-95 in water, % | 0.333 | 0.500 | 0.333 | | 0.333 | 0.333 | 0.250 | 0.333 | 0.333 | 0.333 |
| EMA® Resin in water, 1% | | | | 0.333 | | | | | | |
| Relative Viscosity | 1.66 | 1.73 | 1.60 | 1.72 | 1.41 | 1.53 | 1.64 | 1.34 | 1.61 | 1.63 |
| K Value | 49.6 | 51.8 | 47.3 | 51.3 | 39.5 | 44.6 | 48.5 | 35.6 | 47.8 | 48.4 |
| Molecular Weight × $10^{-3}$ | 370 | 430 | 480 | 440 | 380 | 260 | 500 | 120 | 570 | 550 |
| Acid Number | 129.4 | 120.0 | 124.3 | 143.5 | 142.8 | 131.0 | 135.4 | 138.7 | 123.3 | 132.3 |
| Tg, °C. | 70 | 73 | 71 | 69 | 51 | 72 | 79 | 79 | 72 | 86 | bon $C_3$–$C_4$ propellant. The resins were each dissolved in anhydrous ethanol, 100% neutralized with 2-amino-2-methyl-1-propanol (AMP) and charged to an aerosol spray can with a hydrocarbon propellant A-46 (blend of 80/20 propane/isobutene), as noted in following Table III.

TABLE III

|  | Formulation A | | Formulation B | |
| --- | --- | --- | --- | --- |
|  | Wt., g. | Wt. % | Wt., g. | Wt. % |
| Resyn ® 28-2930 (control) | 2.5 | 2.5 | — | — |
| Hair spray resins of this invention | — | — | 2.5 | 2.5 |
| Anhydrous ethanol (SDA 40-2) | 67.5 | 67.5 | 67.5 | 67.5 |
| Propellant A-46 | 30.0 | 30.0 | 30.0 | 30.0 |
| 2-Amino-2-methyl-1-propanol (AMP) | ** | ** | ** | ** |

**As required to 100% neutralization of the carboxyl functionalities of the hair spray resin.

The aerosol hair sprays thus obtained were evaluated for their hair holding properties. The clean, dried tresses were each sprayed with the above formulations 3 seconds at a distance of 2 inches, combed through twice, rolled on ⅝" roller and dried under a salon type drier for one hour. These tresses were then unrolled on a humidity rack and placed in a 80° F., 90% relative humidity cabinet for 90 minutes. The curl readings at 60 and 90 minutes were recorded. The results of the relative curl retention at 60 and 90 minutes intervals, using Resyn ® 28-2930 as the control which is assigned as a value of 1.00, are shown in the following TABLE IV.

TABLE IV

| Hair Spray Resin | Curl Retention Relative to Resyn ® 28-2930*** | |
| --- | --- | --- |
|  | 60 minutes | 90 minutes |
| Resyn ® 28-2930 (control) | 1.00 | 1.00 |
| Polymer 1 | 1.09 | 1.09 |
| Polymer 2 | 1.09 | 1.12 |
| Polymer 3 | 1.30 | 1.16 |
| Polymer 4 | 1.09 | 1.10 |
| Polymer 5 | 1.01 | 1.03 |
| Polymer 6 | 1.06 | 1.03 |
| Polymer 7 | 1.23 | 1.13 |
| Polymer 8 | 1.05 | 1.02 |
| Polymer 9 | 1.14 | 1.16 |
| Polymer 10 | 1.14 | 1.13 |

***Differences of 0.10 or greater represent significant differences in hair holding performance.

The above data show that the vinyl acetate/mono-n-alkyl maleate/isobornyl acrylate and vinyl acetate/mono-n-alkyl maleate/isobornyl methacrylate polymers of this invention are significantly superior in high humidity holding (60 and 90 minute intervals at 80° F. and 90% relative humidity) to a commercial hair spray resin such as Resyn ® 28-2930.

After curl retention tests were completed, each of the polymer films was easily removed in aqueous soap solutions or shampoos, leaving no detectable residues.

EXAMPLE 13 (COMPARATIVE)

As taught in the art by Example 7 of U.S. Pat. No. 4,567,035, equimolar amounts of vinyl acetate and monoethyl maleate in a solution (ethanol) polymerization process failed to form the desired vinyl acetate/monoethyl maleate alternating copolymer for use as the hair spray resin. The following example was carried out to demonstrate that the suspension polymerization of vinyl acetate and mono-n-butyl maleate in water also failed to produce the discrete, microspheric resins suitable for use as the hair spray resins. Mono-n-butyl maleate was substituted for monoethyl maleate since the later is soluble in water and is not suitable for the suspension polymerization method.

A vinyl acetate/mono-n-butyl maleate copolymer (Polymer 11) with a molar ratio of vinyl acetate (0.8 mole) and mono-n-butyl maleate (0.6 mole), identical to the Polymer 7, was prepared under the polymerization conditions of foreqoinq Example 7, except no bicyclic ester, isobornyl acrylate or isobornyl methacrylate, or a mixture thereof was incorporated. The resultant polymer was a sticky, elastic mass containing unreacted monomers and thus was not suitable for hair spray applications.

This example establishes that the incorporation of the present bicyclic ester monomer, e.g. isobornyl acrylate, exo-norbornyl acrylate, endo-norbornyl acrylate, isobornyl methacrylate, exo-norbornyl methacrylate, endo-norbornyl methacrylate or a mixture thereof in amounts within the above ranges, is essential in this invention to provide the present products having excellent solubility in ethanol/hydrocarbon propellant mixture and excellent hair holding, as shown in Examples 11–12.

EXAMPLE 14 (COMPARATIVE)

As discussed above, it is essential in the preparation of the polymers of the present invention by a suspension polymerization method that their molecular weights are sufficiently high to provide superior curl retention but insufficient to cause nozzle clogging in the dispenser. The following experiment was carried out to establish that the solution polymerization in ethanol failed to provide the adequate molecular weight of this invention.

To a one-liter glass resin kettle was added a reactant mixture of 68.80 g. of vinyl acetate (0.8 mole), 103.20 g. of mono-n-butyl maleate (0.6 mole), 16.64 g. of isobornyl acrylate (0.08 mole), 188.64 g. of anhydrous ethanol and 2.52 g. of di-(2-ethylhexyl)peroxydicarbonate (Lupersol ® 223 M75 75% active) and the mixture was stirred at 60° C. for 16 hours. The final product (Polymer 12) in ethanol was recovered and had a solids content of 48.90%, a relative viscosity of 1.07 and a K value of 15. The curl retention of Polymer 12 was inferior to the same polymer (i.e. Polymer 7) having a K value of 48.5, prepared by the suspension polymerization method. A comparison of curl retention capability is summarized below in Table V.

TABLE V

| Hair Spray Resin | Curl Retention Relative to Resyn ® 28-2930* | | |
| --- | --- | --- | --- |
|  | K Value | 60 Minutes | 90 Minutes |
| Resyn ® 28-2930 (control) | 40 | 1.00 | 1.00 |
| Polymer 7 | 48.5 | 1.23 | 1.13 |
| Polymer 12 | 15 | 0.65 | 0.69 |

*Differences of 0.10 or greater represent significant difference in hair holding performance.

EXAMPLE 15 (COMPARATIVE)

The following example compares the clear/cloud temperatures, relative viscosities and spray patterns of the present resins with the commercial hair spray resin, Resyn ® 28-2930. In all cases, the clear/cloud temperature was determined on 2.5% resin in anhydrous ethanol and the relative viscosities were determined on 1.0% resin in anhydrous ethanol. For spray pattern determinations, each composition was formulated with 2.5 parts of resin (100% neutralized with 2-amino-2-methyl-1-propanol), 67.5 parts of anhydrous ethanol and 30 parts of hydrocarbon propellant A-46 (blend of 20/80 propane/isobutane). The spray patterns from aerosol bottles fitted with a Mistettle I (Calmar) valve were recorded on alcohol-sensitive paper (Permapaper from Hewlett Packard Corporation) and results reported in following Table VI.

TABLE VI

| Hair Spray Resin | Relative Viscosity (K value) | | Clear/Cloud Temp., °F. | Spray Pattern |
|---|---|---|---|---|
| Polymer 1 | 1.66 | (49.6) | below 0° F., both | Fine, disperse spray |
| Polymer 2 | 1.73 | (51.8) | below 0° F., both | Fine, disperse spray |
| Polymer 3 | 1.60 | (47.3) | below 0° F., both | Fine, disperse spray |
| Polymer 4 | 1.72 | (51.3) | below 0° F., both | Fine, disperse spray |
| Polymer 5 | 1.41 | (39.5) | below 0° F., both | Fine, disperse spray |
| Polymer 6 | 1.53 | (44.6) | below 0° F., both | Fine, disperse spray |
| Polymer 7 | 1.64 | (48.5) | below 0° F., both | Fine, disperse spray |
| Polymer 8 | 1.34 | (35.6) | below 0° F., both | Fine, disperse spray |
| Polymer 9 | 1.61 | (47.8) | below 0° F., both | Fine, disperse spray |
| Polymer 10 | 1.63 | (48.4) | below 0° F., both | Fine, disperse spray |
| Resyn ® 28-2930 | 1.21 | (28.0) | 18/23° F. | Fine, disperse spray |

The hair spray resins of the present invention deliver the desired fine, disperse spray pattern without nozzle clogging and generally have a viscosity higher than the commericial hair spray resin Resyn® 28-2930. Furthermore, their solubilities are superior to the above commericial hair spray resin as indicated by their low clear/cloud temperatures. Also, no corrosion of the spray container was noted for the polymers of the present invention.

TABLE 16 (COMPARATIVE)

This example illustrates that the resin film of this invention (Polymer 7) is non-tacky under relatively high humidity conditions and is superior to the commercial hair spray resin Resyn® 28-2930.

Each hair spray resin was dissolved in ethanol (5%) and neutralized with 2-amino-2-methyl-1-propanol (AMP) to a level commonly found in commercial hair spray formulations—namely, Polymer 7, 10% and Resyn® 28-2930, 90%. Each resin solution was then sprayed evenly (18 shots) on glass plates, using aerosol bottles fitted with a Mistettle I (Calmar) valve. After drying in air, three cotton balls were gently placed on each test area, and the plates transferred to a preconditioned humidity cabinet (temperature at 70° and 80° F. and % relative humidity at 80% and 90%). At 20 minute intervals, one of the three cotton ball was pressed onto the film and then pulled away. The film tackiness was determined from the amount of cotton fiber retained by the film and was rated as NT (no tack), ST (slight tack), or T (significant tack). The results of these experiments are reported in Table VII.

TABLE VII

| TESTING CONDITIONS | POLYMER 7 | RESYN ® 28-2930 |
|---|---|---|
| 70° F./80% RH | | |
| 20 min. | NT | NT |
| 40 min. | NT | NT |
| 60 min. | NT | NT |
| 80° F./90% RH | | |
| 20 min. | NT | T |
| 40 min. | NT | T |
| 60 min. | NT | T |

EXAMPLE 17

This example demonstrates that the hair spray resins of the present invention exhibit excellent water compatibility and thus significantly reduced flammability in both pump and aerosol hair-spray applications.

Hair spray resin, Polymer 7, (3.0 parts) was dissolved in ethanol, (SDA 40-2), (15 parts), neutralized with 2-amino-2-methyl-1-propanol, (0.50 parts) and blended with 81.5 parts of distilled water.

The clear solution thus obtained contains a 50% neutralized resin and is suitable for pump spray applications. When sprayed on the dry, clean tresses, the clear resin solution produced a non-tacky, clear, transparent film.

All of the products of this invention are non-corrosive to metal containers and their viscosities remain unchanged over long periods such that nozzle plugging in the normal life of an aerosol dispenser is avoided. It is to be understood that other species of vinyl ester and maleate half esters mentioned in the foregoing disclosure and other bicyclic esters or mixtures thereof including the exo- and endo-norbornyl acrylates or methacrylates or any intermixture of the present bicyclic esters can be substituted in the above examples to provide resin beads having improved solubility, propellant compatibility and curl retention.

What is claimed is:

1. A terpolymer monomers (a) a vinyl ester; (b) a water insoluble or water miscible alkyl maleate half ester and (c) an acrylate or methacrylate ester of a saturated, hydroxylated, bicyclic hydrocarbon in a molar ratio of (a) to (b) to (c) of about 1:0.35–1:0.05–0.25.

2. The terpolymer of claim 1 wherein said vinyl ester is vinyl acetate and said acrylate or methacrylate monomer is isobornyl acrylate isobornyl methacrylate or a mixture thereof.

3. The terpolymer of claim 2 wherein said alkyl maleate half ester is mono-n-butyl maleate, mono-n-pentyl maleate or a mixture thereof.

4. The terpolymer of claim 1 wherein said terpolymer is vinyl acetate/mono-n-butyl maleate/ an isobornyl acrylate in a molar ratio of about 1:0.6–0.8:0.08–0.12.

5. The process of adding a sufficient alcohol solubilizing and hair fixing amount of the terpolymer of claim 1 to an inert carrier formulation containing an alcohol suitable for use in a hair spray.

6. The process of adding a sufficient alcohol solubilizing and hair fixing amount of the terpolymer of claim 3 to an inert carrier in a formulation suitable for use in a hair spray.

7. The process of claim 6 wherein the hair spray formulation contains a mixture of an alcohol and a hydrocarbon carrier.

8. The process of claim 7 wherein said carrier is a mixture of ethanol, propane and isobutane and said formulation contains a propellant suitable for use in a hair spray.

9. The process of claim 5 wherein the terpolymer is employed at a concentration of between about 0.5% and about 10% solids in a hair spray formulation.

10. The process for producing the terpolymeric resin of claim 1 as discrete microspherical particles which comprises: mixing monomers (a), (b) and (c) in the recited proportions with a low temperature free radical initiator; polymerizing said monomers in an inert suspension medium with constant agitation in a reaction zone maintained at a temperature between about 40° C. and about 90° C. until a microspherical particulate product is formed; separating said particles from the suspension medium and recovering said particles as the product of the process.

11. The process for producing the terpolymeric resin of claim 3 as discrete microspherical particles which comprises: mixing monomers (a), (b) and (c) in the recited proportions with a low temperature free radical initiator; polymerizing said monomers in an inert suspension medium with constant agitation in a reaction zone maintained at a temperature between about 50° C. and about 70° C. until the microspherical particulate product is formed; separating said particles from the suspension medium and recovering said particles as the product of the process.

12. The process of claim 10 wherein said initiator is selected from the group consisting of a peroxyester, a peroxydicarbonate and an azo compound.

13. The process of claim 11 wherein said initiator is selected from the group consisting of tertiary-butyl peroxypivalate, tertiary-amyl-peroxypivalate, tertiary-butylperoxy neodecanoate, tertiary-amyl-peroxy neodecanoate, di-(2-ethylhexyl) peroxydicarbonate, di-(sec-butyl)peroxydicarbonate, di-(n-propyl)peroxydicarbonate, 2,2'-azobis-(2,4-dimethyl-4-methoxy-valeronitrile), and 2,2'-azobis-(2,4-dimethyl-valeronitrile).

14. The process of claim 11 wherein said initiator is tertiary-butyl peroxyneodecanoate or tertiary-butyl peroxypivalate.

15. The process of claim 11 wherein said initiator is di-(2-ethylhexyl)peroxydicarbonate.

16. The process of claim 10 wherein said initiator is employed in a concentration of between about 0.05 and about 5.0 wt. % based on the total monomers of the terpolymer.

17. The process of claim 11 wherein said suspension medium is an aqueous solution of a copolymer selected from the group consisting of methyl vinyl ether/maleic acid copolymer and ethylene/maleic anhydride copolymer.

18. The process of claim 17 wherein the aqueous suspension medium contains between about 0.1 wt. % and about 2.0 wt. % of said copolymer and the total monomers of the terpolymer are in a concentration between about 10 wt. % and about 50 wt. %.

19. The process of applying to hair an effective hair holding amount of the terpolymer of claim 1 in an inert aqueous carrier containing an inert solubilizer.

20. The process of applying to hair an effective hair holding amount of the terpolymer of claim 3 in an inert aqueous ethanol carrier.

* * * * *